(12) United States Patent
Even-Tov et al.

(10) Patent No.: US 6,212,418 B1
(45) Date of Patent: Apr. 3, 2001

(54) METHODS, KITS, ELECTRODES AND COMPOSITIONS FOR ASSESSING THE LEVEL OF AN ANALYTE OF INTEREST IN FLUID SAMPLES

(75) Inventors: Irina Even-Tov, Haifa; Ami Naveh, Megibo; Igor Kuperman, Yokneam, all of (IL)

(73) Assignee: Advanced Monitoring Systems Ltd., Yokneam (IL)

( * ) Notice: Subject to any disclaimer, the term of this patent is extended or adjusted under 35 U.S.C. 154(b) by 0 days.

(21) Appl. No.: 09/116,493

(22) Filed: Jul. 16, 1998

Related U.S. Application Data (63) Continuation-in-part of application No. 08/974,842, filed on Nov. 20, 1997, now Pat. No. 6,061,586.

(51) Int. Cl.[7] .................................................. A61B 5/05
(52) U.S. Cl. ............................ 600/349; 600/573; 600/584
(58) Field of Search .................................. 600/309, 345, 600/349, 362, 573, 584; 604/1, 187; 436/178

(56) References Cited

U.S. PATENT DOCUMENTS 5,676,144  *  10/1997  Schoendorfer ...................... 600/573
5,981,293  *  11/1999  Charlton ............................... 600/573
5,997,519  *  12/1999  Hemstreet et al. ................... 600/573
6,032,059  *   2/2000  Henning et al. ...................... 600/573

* cited by examiner

*Primary Examiner*—Cary O'Connor
*Assistant Examiner*—Ryan Carter
(74) *Attorney, Agent, or Firm*—Mark M. Friedman (57) ABSTRACT

A potentiometric method for determining low concentration of an analyte of interest present in a fluid sample in a concentration optionally below its linear range of detection in a presence of at least one interfering substance of known concentration the method is effected by following the steps of (a) adding to the sample a predetermined amount of the analyte of interest, such that a total concentration of the analyte of interest present in the sample is within the linear range of its detection; (b) providing an analyte selective electrode being selective to the analyte of interest and a reference electrode both electrodes being equilibrated with a solution including the at least one interfering substance in concentration similar to said known concentration; (c) contacting the analyte selective electrode and the reference electrode with the sample; (d) measuring a signal representative of a potential drop between the analyte selective electrode and the reference electrode; and (e) using the signal for determining the concentration of the analyte of interest present in the fluid sample prior to the addition of the predetermined amount of the analyte of interest.

29 Claims, 3 Drawing Sheets

METHODS, KITS, ELECTRODES AND COMPOSITIONS FOR ASSESSING THE LEVEL OF AN ANALYTE OF INTEREST IN FLUID SAMPLES

This is a continuation-in-part or U.S. patent application Ser. No. 08/974,842, filed Nov. 20, 1997, now U.S. Pat. No. 6,061,586.

FIELD AND BACKGROUND OF THE INVENTION

The present invention relates to analytical methods, kits, electrodes and compositions for analysis of analytes in fluid samples. More particularly, the present invention relates to methods, kits, electrodes and compositions for detection of an analyte of interest in a clinical sample, and principally to compositions, methods, kits and electrodes useful in the analysis of lithium in saliva and further in sera, plasma, urine, cerebro-spinal fluid, whole blood or other biological (clinical) fluids, utilizing potentiometric ion selective electrodes.

Lithium, usually in the form of lithium carbonate or other lithium salts, is commonly used for the treatment of manic, manic depressive, hyper active, violent patients, etc. Although traces of lithium ion are distributed widely throughout the body, the major effect of exogenous lithium is upon the central nervous system (CNS).

Unlike other antipsychotic pharmaceutical agents, lithium is not thought to possess any general sedative properties, and, in therapeutic amounts, CNS effects are not observed except during chronic administration of lithium in manic or manic-depressive patients.

The exact therapeutic mechanism of lithium is not currently known, primarily because the pathophysiology of manic disorders is unknown.

Lithium ions are readily absorbed when given orally, and a plasma lithium peak is reached approximately 2–4 hours after ingestion of lithium carbonate. Lithium plasma levels are usually monitored at least twice weekly in new patients in order to maintain the level thereof within the range of from about 0.2 to about 1.0 mmole per liter. For severe cases of mania, however, the lithium plasma level may be increased to about 1.5 mmole per liter.

Therapeutic doses of lithium can cause fatigue, muscular weakness, slurred speech, ataxia, tremor of the hands, nausea, vomiting, diarrhea and thirst. At plasma levels above about 2.2 mmole per liter, more serious toxic effects occur, with the CNS primarily affected, i.e., consciousness is impaired, coma may occur, muscular rigidity, hyperactive deep reflexes and marked tremor and muscular fasciculations are observed, epileptic seizures can occur, and EEG abnormalities are common. A lithium plasma level of about 3.0 mmole per liter can be fatal.

Accordingly, it is not only important, but essential, to know what such plasma level is in order to avoid the deleterious effects associated therewith.

Analysis of lithium in biological fluids, such as sera, plasma, urine, cerebro-spinal fluid, or whole blood, is hampered by the presence of other ionic compounds in such fluids, and in particular, sodium ions. Analysis of lithium in saliva is particularly hampered by the presence of high calcium concentrations, which is present in much lower concentrations in the biological fluids listed above. These interferences are most noticeable at lower lithium concentrations (for example, about 0.10 mmole per liter).

With respect to serum of non-treated individuals, the molar ratio of lithium to sodium is about 1:1500. With respect to saliva, the molar ratio of lithium to calcium is about 1:1000. Accordingly, one of the challenges facing those developing an assay method for lithium is to overcome the interference from such ions.

Flame photometry is one method for lithium analysis in clinical specimens. In flame photometry, atoms are excited to an energy level above their ground state by a flame. Upon return to ground state, the energy is released as radiation at a frequency characteristic of the element under investigation. By measuring the emission light intensity, the concentration of the analyte of interest in the sample can be determined.

Despite its relative simplicity, flame photometry is a tedious procedure and includes several critical disadvantages as an analytical method, e.g., spectral interference between two or more substances in a sample (such as in the case with serum sodium and lithium or saliva calcium and lithium), background interferences, anionic and cationic interferences, and self-absorption.

Furthermore, routine maintenance of the instrumentation is not only critical to ensure good analytical results, but is itself a tedious procedure. Additionally, flame photometry instruments utilize air compressors, which on the whole are noisy, a distinct disadvantage in a clinical setting.

Finally, there is the practical concern of safely storing a flammable gas in a laboratory environment.

Thus, currently, the monitoring of lithium concentration within the blood involves a lengthy procedure which requires the employment of expensive non-safe equipment and professional operators for operating such equipment. A blood sample is extracted from the patient by a family doctor or a nurse. The extracted blood is collected within a sample tube. Following the addition of an anti-clotting material, the sample tube is transferred to a laboratory for analysis. At the laboratory, the plasma of the blood sample is separated from the blood cells by means of a centrifuge. The plasma is then transferred to another tube and is then analyzed by means of a flame photometer. The flame photometer is an expansive and cumbersome device which requires a professional operator. Further, the flame photometer is expensive to operate and has to be specifically prepared and calibrated prior to each examination. As a result, such device is usually activated only once or twice a week, after a substantial amount of blood samples have been collected. Following analysis of the blood sample, a written result is sent to the office and then to the family doctor. Such lengthy process (which may be extended for more than one week) may be ineffective in the sense that it does not provide an immediate feedback in the event of toxicity. Toxic levels of lithium within the patient's blood may occur as a result of introduction of over-dosage of the drug, or in the event of impaired clearance of the drug owing to damaged kidney or damaged liver. Lithium concentration within the blood is also dependent on hormonal regulation and other physiological factors and therefore may feature abnormal profile when the patient suffers from hormonal or other physiological problems. An immediate feedback is extremely important when treating children since relatively low concentrations of lithium may cause toxicity. Since there is no current effective treatment for lithium poisoning, an immediate feedback relating to lithium concentration within the blood is essential.

Ion selective electrode (ISE) technology is an alternative to flame photometry which avoids many of these problems.

ISE technology involves the use of a reference electrode and an ion selective electrode separated by a membrane. The ion selective electrode is specific or sensitive to the particular ion of interest. Typically, the reference electrode and the ion selective electrode are simultaneously immersed into a sample solution. An electrical potential is developed between the electrodes which is relative to the presence of the ion to which the ISE is sensitive or specific. This potential can be utilized to determine the concentration of that ion in the sample. Most often the investigator desires to only measure the concentration of one ion out of the many different ions in solution. Thus, the ion selective composition of the ISE, referred to as a "carrier" or "ionophore", must be capable of sequentially complexing the desired ion, transporting the complexed ion across the membrane, and releasing the ion in preference to all other ions which may be present in the sample solution.

Macrocyclic polyethers, also referred to as cryptanols or "crown ethers", are well known lithium ion-complexing compounds which are suitable for use as ion selective electrodes. Such ionophores are described in, for example, U.S. Pat. Nos. 4,214,968; 4,504,368; Oesch, U. et al., "Ion Selective Membrane Electrodes for Clinical Use", Clin. Chem. 32:1448–1459 (1996); Kitayama, S. et al. "Lithium-Selective Polymeric Electrodes Based on Dodecylmethyl-14-Crown-4", Analyst 110:295–299 (1985); and, Attiyat, A. et al., "Comparative Evaluation of Neutral and Proton-Ionizable Crown Ether Compounds as Lithium in Ion-Selective Electrodes and in Solvent Extraction", Anal. Chem. 60:2561–2564 (1988). Other lithium ion complexing compounds are also available, and examples of these are described in U.S. Pat. No. 4,853,090; Gadzekpo, V. P. Y. et al., "Lipophilic Lithium Ion Carrier in a Lithium Ion Selective Electrode", Anal. Chem. 57:493–495 (1985); and, Gadzekpo, V. P. Y. et al., "Problems in the Application of Ion-Selective Electrodes to Serum Lithium Analysis", Analyst, 111:567–570 (1986). All of the preceding references of this paragraph are incorporated herein by reference as if fully set forth herein. Carriers or ionophores specific to ions other than lithium and to a variety of drugs are also well known in the art. Examples include, but are not limited to, calcium ionophore III (A23187 calcimicine). All of the preceding references of this paragraph are incorporated herein by reference as if fully set forth herein.

Two methods are associated with ISE: the direct potentiometric method, where the sample is measured directly; and the indirect potentiometric method, where the sample is diluted prior to analysis. Of the two, the indirect potentiometric method is in some aspects preferred because: (a) dilution of the sample derives the advantages of mass action law, (b) serum results do not usually correlate well between flame photometry and the direct potentiometric method, and (c) maintenance of a direct ISE analyzer is more difficult than an indirect ISE due to protein build-up on the direct ISE.

However, despite the advantages of the indirect potentiometric methodology, there are no indirect potentiometric analyzers for lithium commercially available. This is based, in part, on the relationship of lithium in a clinical specimen to other ions therein. For example, in serum, where as previously noted the ratio of lithium to sodium is 1:1500, or in saliva, where as previously noted the ratio of lithium to calcium is 1:1000. Furthermore, dilution of a sample makes analysis of the already miniscule amount of lithium present very difficult.

U.S. Pat. Nos. 5,110,742 and 5,288,678 teach indirect potentiometric method and diluent for analysis of lithium. The diluent includes effective amounts of a pH buffer and a non-cationic surfactant comprising at least one hydrophobic group, at least one hydrophilic group and being substantially free of polyoxyethylene groups. The pH buffer is preferably tris-(hydroxymethyl) aminomethane-phosphate, and the surfactant is 2,4,9,7-tetramethyl-5-decyn-4,7 diol. An indirect potentiometric determination of lithium in a clinical sample comprises according to U.S. Pat. Nos. 5,110,742 and 5,288,678 the steps of mixing the sample with a diluent, contacting an aliquot of the diluted sample with a lithium specific ion selective electrode and at least one ion selective electrode specifically responsive to a monovalent interfering ion, and measuring both the response of the lithium specific ion selective electrode and the monovalent interfering ion specific ion selective electrode, the responses being an indication of the concentration of lithium in the sample.

This method suffers a disadvantage, because two or more ions are to be measured instead of a single ion of interest. This calls for a plurality of sample electrodes being employed, each has to be calibrated before use, etc. Furthermore, this method is not applicable for saliva lithium determinations because the major interfering ion in saliva is the divalent ion calcium.

Indeed, it was thus far never attempted nor was it suggested to specifically monitor lithium concentration is saliva using potentiometric methods, either direct or indirect. However, being completely non-invasive, there is a long felt need for potentiometric methods adapted for saliva lithium determinations.

It is well known that any ISE is characterized by a given range of concentrations in which the potential between the ISE and the reference electrode is proportional to the concentration. This range is typically referred to as the linear range. Measurements of concentrations outside the linear range are either non-informative because of unavailability of a connecting function or grossly inaccurate. This phenomenon is even intensified in the presence of interfering ions, especially if present at relative high concentrations. The prior art fails to teach effective strategies of measuring ion concentrations falling below the linear range of their respective ISE.

Thus, a need exists for a simple and reliable potentiometric method for the determination of lithium in clinical samples, especially in saliva.

SUMMARY OF THE INVENTION

According to the present invention there is provided a potentiometric method for determining the concentration of an analyte of interest present in a fluid sample in a concentration optionally below its linear range of detection comprising the steps of (a) adding to the sample a predetermined amount of the analyte of interest, such that the total concentration of the analyte of interest present in the sample is within the linear range of its detection; (b) contacting an analyte selective electrode being selective to the analyte of interest and a reference electrode with the sample; (c) measuring a signal representative of a potential drop between the analyte selective electrode and the reference electrode; and (d) using the signal for determining the concentration of the analyte of interest present in the fluid sample prior to the addition of the predetermined amount of the analyte of interest.

According to further features in preferred embodiments of the invention described below, there is provided a potentiometric method for determining the concentration of an analyte of interest present in a sample in the presence of at least one interfering substance(s) of known concentration(s), the method comprising the steps of (a) providing an analyte selective electrode being selective to the analyte of interest and a reference electrode, both electrodes being equilibrated with a solution including the interfering substance(s) in concentration(s) similar to their known concentration(s) in the sample; (b) contacting the analyte selective electrode and the reference electrode with the sample; (c) measuring a signal representative of a potential drop between the analyte selective electrode and the reference electrode; and (d) using the signal for determining the concentration of the analyte of interest present in the fluid sample.

According to further features in preferred embodiments of the invention described below, there is provided a potentiometric method for determining the concentration of an analyte of interest present in a fluid sample in a concentration optionally below its linear range of detection in the presence of at least one interfering substance(s) of known concentration(s) comprising the steps of (a) adding to the sample a predetermined amount of the analyte of interest, such that the total concentration of the analyte of interest present in the sample is within the linear range of its detection; (b) providing an analyte selective electrode being selective to the analyte of interest and a reference electrode both being equilibrated with a solution including the interfering substance(s) in concentration(s) similar to their known concentration(s) in the sample; (c) contacting the analyte selective electrode and the reference electrode with the sample; (d) measuring a signal representative of a potential drop between the analyte selective electrode and the reference electrode; and (e) using the signal for determining the concentration of the analyte of interest present in the fluid sample prior to the addition of the predetermined amount of the analyte of interest.

According to further features in preferred embodiments of the invention described below, there is provided a device useful in executing a potentiometric method for determining the concentration of an analyte of interest present in a fluid sample in a concentration optionally below its linear range of detection by the potentiometric method, the device comprising a container including a predetermined amount of the analyte of interest, such that when the fluid sample is added to the container a total concentration of the analyte of interest present in the sample is within the linear range of its detection.

According to further features in preferred embodiments of the invention described below, there is provided an equilibrating and maintaining composition for equilibrating and maintaining an analyte selective electrode and a reference electrode, the electrodes being designed to determine a concentration of an analyte of interest in a fluid sample including known concentration(s) of at least one interfering substance(s), the composition comprising the interfering substance(s) in concentration(s) similar to their known concentration(s) in the sample.

According to further features in preferred embodiments of the invention described below, there is provided a kit useful in executing a potentiometric method for determining the concentration of an analyte of interest present in a fluid sample in a concentration optionally below its linear range of detection by the potentiometric method, the sample including known concentration(s) of at least one interfering substance(s), the kit comprising (a) a first container including a predetermined amount of the analyte of interest, such that when the fluid sample is added to the container the total concentration of the analyte of interest present in the sample is within the linear range of detection; and (b) a second container including an equilibrating and maintaining composition for equilibrating and maintaining an analyte selective electrode and a reference electrode, the electrodes being designed to determine the concentration of the analyte of interest in the fluid sample, the composition including the interfering substance(s) in concentration(s) similar to their known concentration(s) in the sample.

According to further features in preferred embodiments of the invention described below, there is provided an analyte selective electrode being designed to determine the concentration of an analyte of interest in a fluid sample including known concentration(s) of at least one interfering substance(s) comprising an electrode body supplemented with an ionophore designed for specifically trapping or transferring the analyte, the electrode being equilibrated with an equilibrating composition including the interfering substance(s) in concentration(s) similar to their known concentration(s) in the sample.

According to further features in preferred embodiments of the invention described below, there is provided a set of electrodes comprising an analyte selective electrode being designed to determine the concentration of an analyte of interest in a fluid sample including known concentration(s) of at least one interfering substance, and a reference electrode, the analyte selective electrode including an electrode body supplemented with an ionophore designed for specifically trapping or transferring the analyte, the electrodes being equilibrated with an equilibrating composition including the interfering substance(s) in concentration(s) similar to their known concentration(s) in the sample.

According to still further features in the described preferred embodiments the fluid sample is a clinical sample.

According to still further features in the described preferred embodiments the clinical sample is selected from the group consisting of saliva, sera, plasma, urine, cerebrospinal fluid and whole blood.

According to still further features in the described preferred embodiments the predetermined amount of the analyte of interest is added to the sample in a dry form.

According to still further features in the described preferred embodiments the analyte of interest is lithium ion.

According to still further features in the described preferred embodiments adding the predetermined amount of the analyte of interest to the sample is effected by pouring the sample into a container including the predetermined amount of the analyte of interest is the dry form.

According to still further features in the described preferred embodiments the analyte of interest is lithium ion.

According to still further features in the described preferred embodiments the predetermined amount of the analyte of interest is in a dry form and is dissolvably adhered to the container.

According to still further features in the described preferred embodiments a predetermined amount of at least one substance selected from the group consisting of anti-foam, detergent, surfactant and buffer is further added to the sample along with the added analyte.

According to still further features in the described preferred embodiments the interfering substance(s) of known concentration(s) are selected from the group consisting of magnesium, potassium, sodium, calcium and combinations thereof.

According to still further features in the described preferred embodiments the equilibrating and maintaining composition comprising about 2–40 mmole per liter calcium ions, about 0.2–4.0 mmole per liter magnesium ions, about 10–50 mmole per liter potassium ions and about 2–20 mmole per liter sodium ions, the composition is for determining a concentration of an analyte of interest in a saliva sample.

According to still further features in the described preferred embodiments the equilibrating and maintaining composition, comprising about 10 mmole per liter calcium ions, about 2.5 mmole per liter magnesium ions, about 40 mmole per liter potassium ions and about 8 mmole per liter sodium ions.

The present invention successfully addresses the shortcomings of the presently known configurations by providing an efficient method of detecting low levels of analytes below the linear range of their detection and in the presence of interfering substances using potentiometric methods.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is of analytical methods, kits, electrodes and compositions which can be used for the detection of an analyte of interest in a fluid sample. Specifically, the present invention is useful in the analysis of lithium in saliva and further in sera, plasma, urine, cerebrospinal fluid, whole blood or other biological fluids utilizing a potentiometric lithium selective electrode.

The principles and operation of the methods, kits, electrodes and compositions according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Although the invention is herein described with particular reference and examples to lithium concentration, it may be used for assessing the concentration of any chemical component within any physiological fluid of the patients (e.g., lymphatic fluid) based on dedicated selective electrodes and given mathematical relationships.

Before turning to a detailed description of the invention, attention is first called to an apparatus described in U.S. patent application Ser. No. 08/947,842, filed Nov. 20, 1997, which is incorporated by reference as if fully set forth herein, which apparatus assisted with the kits, electrodes and compositions of the present invention may be employed while implementing the methods of the present invention.

Figure 1:
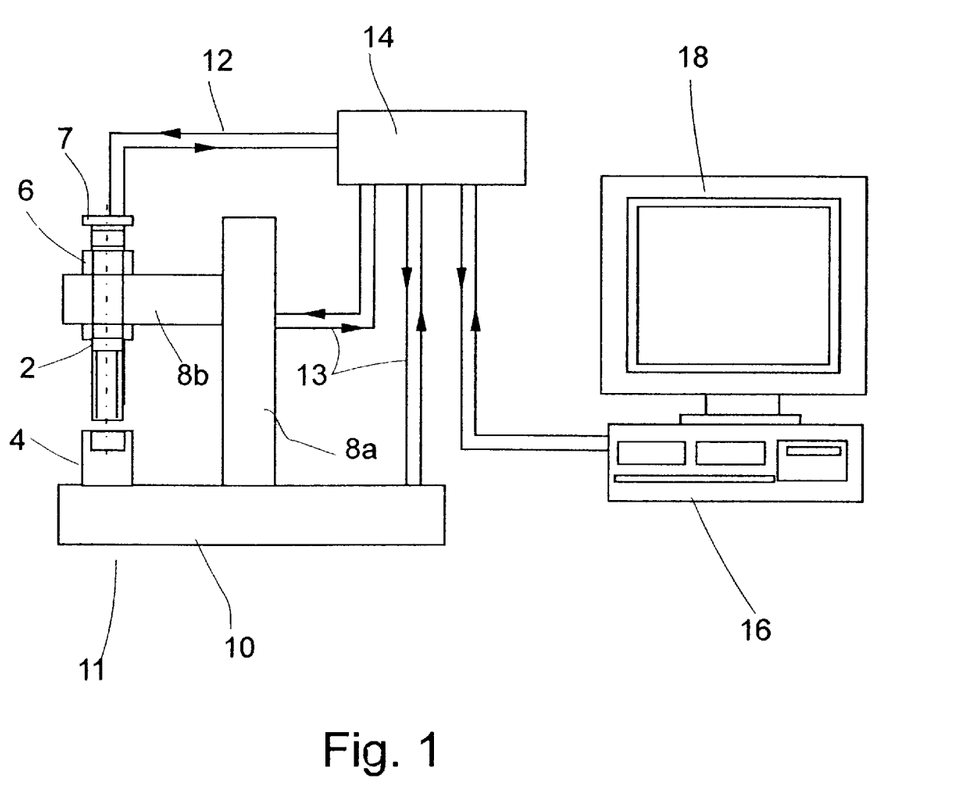
FIG. 1 is a schematic view of a device according to the present invention.
Figure 2:
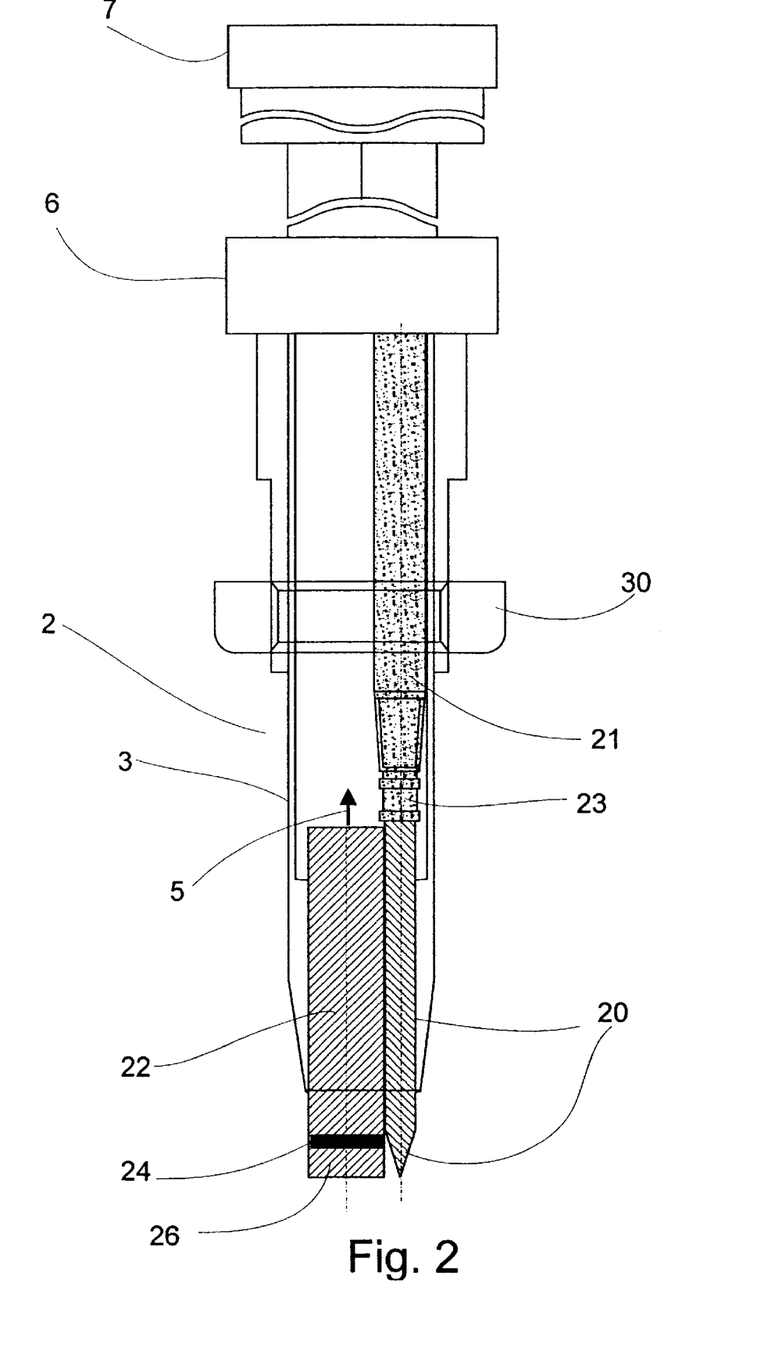
FIG. 2 is an enlarged view of an electrode assembly according to the present invention.

Referring now to the drawings, FIGS. 1 and 2 illustrate a device suitable for implementing the methods of the present invention. The device includes an electrode assembly 2 for measuring the concentration of a chemical component such as lithium within a patient's saliva according to the potential drop measured between an ion selective electrode 22 and a reference electrode 20, wherein ion selective electrode 22 specifically bind the chemical component.

As shown in FIG. 2, ion selective electrode 22 and reference electrode 20 are accommodated within a housing 3 and are immersed within a cup or container 4 containing a saliva sample from a patient. Reference electrode 20 is preferably connected to a container 21 including a reference solution by means of a connector element 23. Container 21 is preferably held within housing 3 by means of an electrode holder 30. Ion selective electrode 22 preferably includes a selective membrane 26 which specifically enables the passage of lithium therethrough, the membrane being connected to ion selective electrode 22 by means of a solid contact connector 24. As shown, ion selective electrode 22 is preferably inserted into housing 3 as indicated by arrow 5.

Methods for manufacturing ion selective electrodes are well known to those skilled in the art and will not be set forth in detail here. Reference is made to U.S. Pat. Nos. 4,770,759 and 4,853,090 which are incorporated herein by reference. A preferred lithium ionophore is 6,6 dibenzyl-14-crown-4 ether.

Electrode assembly 2 further includes a processing element 6 for initial processing of the voltage signal obtained by the potential drop measured between ion selective electrode 22 and reference electrode 20. Processing element 6 preferably includes an amplifier for amplifying the voltage signal and an analog to digital converter for converting such analog voltage signal to a digital signal. In addition, electrode assembly 2 further includes an interface 7 for connecting electrode assembly 2 to a microprocessor 16 by means of electrical wires 12.

As shown in FIG. 1, electrode assembly 2 is preferably held at a predetermined height above cup 4 by means of a stand element 11. Stand element 11 preferably includes a holding member 8b for holding electrode assembly 2, the holding member being movable along a shaft member 8a anchored to a support member 10. Cup 4 is positioned on support member 10 so as to allow immersion of ion selective electrode 22 and reference electrode within the patient's saliva.

Preferably, stand 11 includes an automatically operated mechanical system. Accordingly, holding member 8b and shaft member 8a as well as support member 10 are preferably electrically connected to microprocessor 16 by means of electrical wires 13 so as to allow automatic handling of member 8b with reference to support member 10, thereby accurately positioning electrode assembly 3 above cup 4 and appropriately immersing electrodes 20 and 22 within the patient's saliva.

Microprocessor 16 preferably includes a software card (schematically denoted as 14) for manipulating the device according to predetermined requirements. Specifically, software card 14 may include various algorithms for calculating the lithium concentration within the patient's blood according to the lithium concentration measured by electrode assembly 2.

As shown in FIG. 1, a device according to the present invention further includes a display element 18 for displaying the results of a current test as well as results of previous tests or any other parameters related to the medical record of a specific patient. An alarm signal may indicate that a toxic level of lithium has been identified, or that a substantially low level of lithium has been identified. The device may further include a printer (not shown) for providing written results.

A preferred algorithm for calculating lithium concentration within a patient's blood according to the lithium concentration measured within the patient's saliva may be as follows: $[Li]_{blood}=0.13+0.36\times[Li]_{saliva}$.

The above mathematical model, which is well known in the art, shows the advantage of saliva tests over blood tests. Specifically, the lithium concentration within a patient's saliva is amplified with relation to the lithium concentration within the patient's blood. Thus, saliva tests may provide greater accuracy relative to blood tests owing to such physiological amplifying effect.

Alternatively, reference measurements of lithium concentrations within the patient's blood and saliva may be conducted so as to determine a specific factor for a specific patient according which future analyses are performed. For example, if according to the reference measurements a factor K is obtained, wherein: $[Li]_{blood}=K\times[Li]_{saliva}$, then such factor is used for assessing future lithium concentrations within the patient's blood based on respective lithium concentrations measured within the patient's saliva.

The device herein described and other similar devices are useful in implementing the methods of the present invention as described hereinunder.

According to one aspect of the present invention, there is provided a potentiometric method for determining low concentration of an analyte of interest present in a fluid sample. The analyte may be any drug or ion, such as lithium, for which an analyte selective electrode is available. The fluid sample can be a clinical sample, such as, but not limited to saliva, sera, plasma, urine, cerebro-spinal fluid and whole blood.

As used herein the term "low" refers to a concentration optionally close or below the linear range of detection using a given detection method.

While executing the method according to the first aspect of the invention, a predetermined amount of the analyte of interest is added to the analyzed sample. This amount is selected such that the total concentration of the analyte of interest present in the sample following the addition as described is within the linear range of its detection using the given detection method. It is important to ensure that the added analyte is well dissolved before executing the following steps of the method of the present invention.

In a second step of the method according to the first aspect of the present invention, an analyte selective electrode (e.g., ion selective electrode, such as lithium selective electrode) being selective to the analyte of interest, and a reference electrode are operatively contacted with the sample, whereas in a third step of the method a signal (e.g., voltage signal) representative of a potential drop between the analyte selective electrode and the reference electrode is measured.

In a fourth step of the method according to this aspect of the invention the signal thus measured is used for determining the concentration of the analyte of interest present in the fluid sample prior to the addition of the predetermined amount of the analyte of interest. To this end, typically, the total concentration of the analyte is determined, and the contribution of the added analyte to the total is thereafter subtracted.

The advantage of the method hereinabove described is in that it enables determination of concentrations well below the accurate or theoretical detection level of the electrodes. This is the case since by the external addition of the analyte, its total concentration falls within the linear range of detection, in which range the voltage signal obtained is substantially proportional to the actual concentration of analyte present in the sample. Within the linear range the measurement is highly accurate, wherein even small concentration shifts are readily detectable.

For example, the linear range of a conventional lithium selective electrode ranges from 0.5–20 mmole per liter. Within this range its accuracy is within ±0.04 mmole per liter. Thus a sample including 0.2 mmole per liter of lithium, which falls well below the linear range of detection, can be accurately measured using the method herein described because following the addition of a predetermined amount of lithium to the sample such that the total concentration of lithium following the addition is, say, 0.9 mmole per liter. For the latter concentration the accuracy of measurement falls within ±0.04 mmole per liter, i.e., well below the initial concentration of the analyte in the sample. Thus, the initial concentration of the analyte in the sample is readily and accurately determined.

The method as described herein is of great advantage when lithium concentrations are to be determined in biological fluids because the natural concentration of lithium in such fluids is close to zero. In lithium treated patients, such low concentrations characterize patients that refrain from taking their lithium medicaments.

Figure 3:
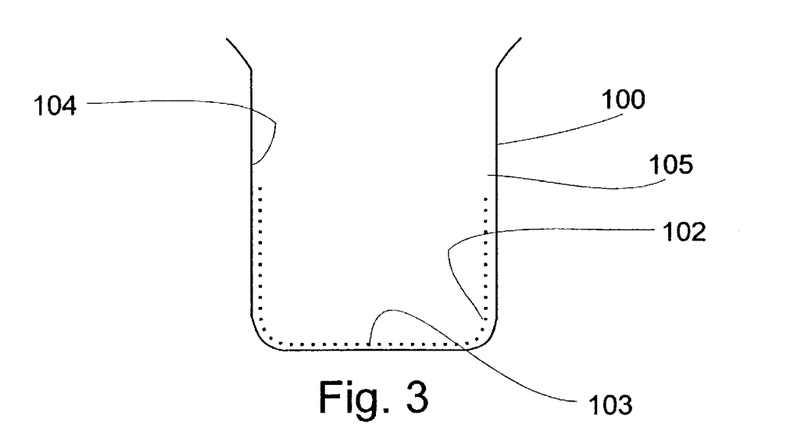
FIG. 3 is a cross sectional view of a container according to the present invention.

With reference now to FIG. 3, according to a preferred embodiment of the present invention the predetermined amount of the analyte of interest is added to the sample in a dry form. Adding the predetermined amount of the analyte of interest to the sample is therefore effected by pouring the sample into a container 100 including the predetermined amount of the analyte of interest 102 in the dry form. Dry form addition of the added analyte to the sample ensures that no dilution takes place, and is therefore advantageous.

Depending on the nature of the sample, according to a preferred embodiment, especially when clinical samples are analyzed, at least one substance of the following is further mixed with the sample, e.g., in a dry form, prior to the measurement: anti-foam, detergent, surfactant and buffer.

The surfactant is preferably a non-cationic surfactant containing at least one hydrophobic group, at least one hydrophilic group and being substantially free of polyoxyethylene groups. Preferably, the pH dictated by the buffer following the addition of the sample is between about 5.5 and about 9.5, more preferably, between about 6.0 and about 7.5. Most preferably, about 7.0. The concentration of the buffer is preferably at least about 0.1 mole per liter, and preferably between about 0.1 mole per liter and about 0.4 moles per liter. The percent by weight of the non-cationic surfactant is at least about 0.005. More preferably, the percent by weight of the non-cationic surfactant is between about 0.01 and about 0.05. Additional features of surfactant and buffer employed are disclosed in U.S. Pat. Nos. 5,110,742 and 5,288,678, which are incorporated by reference as if fully set forth herein.

A container according to the present invention is prepared, for example, by pouring a solution containing the desired predetermined amounts of the desired ingredients into the container, and thereafter removing the fluids therefrom, e.g., by air drying, heat and/or vacuum evaporation, such that the ingredients adhere to the bottom 103 and possibly the inner walls 104 of the container. Such a container is preferably marked by a mark 105 for indicating a user of the amount of fluid sample to be poured therein. Such a container is advantageous because it eliminates the risk of spillage of liquid diluents or non-adhered powders upon use.

According to another aspect of the present invention there is provided a potentiometric method for determining a concentration of an analyte of interest present in a clinical sample in the presence of at least one interfering substance(s) of known concentration(s).

The method is effected by executing the following steps of which, in a first step, an analyte selective electrode being selective to the analyte of interest and a reference electrode, both equilibrated with a solution including the interfering substance(s) in concentration(s) similar to their known concentration(s) are provided.

Thereafter, the analyte selective electrode and the reference electrode are operatively contacted with the sample and a signal representative of a potential drop between the analyte selective electrode and the reference electrode is measured. The signal thus measured is then employed for determining the concentration of the analyte of interest present in the fluid sample.

This aspect of the present invention is of particular advantage when the analyte of interest is present in relatively low concentration as compared with the interfering substances. In sera of lithium carbonate treated patients, for example, the lithium concentration is in the range of 0.2–1.5, whereas the concentration of sodium is about 1500 fold more. Yet, the selectivity of a lithium selective electrode is only about 100–300 fold better for lithium as compared with sodium. As a result, the determination of lithium concentration is greatly affected by the high sodium concentration present in the sample. A similar situation is found in saliva, which include high calcium, potassium and magnesium concentrations. However, by equilibrating the electrodes with the appropriate concentrations of the interfering substances, such as, sodium for serum analysis and calcium for saliva analysis, these ions can no longer affect the measurement.

According to a preferred embodiment of the invention the equilibrating composition is designed to mimic the ions concentrations present in the sample of choice, e.g., saliva, sera, plasma, urine, cerebro-spinal fluid or whole blood.

Thus, further according to the present invention there is provided an equilibrating and maintaining composition for equilibrating and maintaining an analyte selective electrode and a reference electrode, the electrodes being designed to determine a concentration of an analyte of interest in a fluid sample including known concentration(s) of at least one interfering substance(s).

The equilibrating and maintaining composition includes the interfering substance(s) in concentration(s) similar to their known concentration(s) in the sample suspected of including the analyte. The equilibrating and maintaining composition may also serve for washing the electrodes from sample debris after use and for keeping the electrodes between uses.

Yet further according to the present invention there is provided an analyte selective electrode specifically designed at determining a concentration of an analyte of interest in a fluid sample including known concentration(s) of at least one interfering substance(s).

The electrode comprises an electrode body supplemented with an ionophore designed for specifically trapping or transferring the analyte, the electrode is equilibrated with an equilibrating composition including the interfering substance(s) in concentration(s) similar to their known concentration(s) in the sample suspected of including the analyte.

Still further according to the present invention there is provided a set of electrodes. The set includes (i) an analyte selective electrode specifically designed at determining a concentration of an analyte of interest in a fluid sample including known concentration(s) of at least one interfering substance(s) and (ii) a reference electrode. The analyte selective electrode includes an electrode body supplemented with an ionophore designed for specifically trapping or transferring the analyte, whereas both electrodes are equilibrated with an equilibrating composition which includes the interfering substance(s) in concentration(s) similar to their known concentration(s) in the sample suspected of including the analyte.

An equilibrating and maintaining composition which is specifically designed to mimic the ions concentrations characterizing saliva of normal individuals and which is therefore adapted for lithium determinations in lithium treated patients includes about 2–40 mmole per liter, preferably about 10 mmole per liter, calcium ions, about 0.2–4 mmole per liter, preferably about 2.5 mmole per liter, magnesium ions, about 10–50 mmole per liter, preferably about 40 mmole per liter, potassium ions and about 2–20 mmole per liter, preferably about 8 mmole per liter, sodium ions.

Thus far two aspects of the present invention were described in detail. These include (i) the external addition of an analyte to a sample suspected to include a low concentration thereof, so that the total concentration of the analyte in the sample falls within the linear range of detection; and (ii) the equilibrating and maintenance of the electrodes with a composition designed to mimic the concentrations of interfering substances present in the examined sample.

According to a third and presently preferred aspect of the invention, the first and second aspects are combined to provide a potentiometric method for determining low concentration of an analyte of interest present in a fluid sample in a concentration optionally below its linear range of detection in the presence of at least one interfering substance(s) of known concentration(s).

The method is effected by executing the following method steps in which, in a first step, a predetermined amount of the analyte of interest is added to the sample, such that the total concentration of the analyte of interest present in the sample is within the linear range of detection.

Then, an analyte selective electrode being selective to the analyte of interest and a reference electrode are provided, both are equilibrated with a solution including the interfering substance(s) in concentration(s) similar to their known concentration(s) in the sample.

Thereafter, the analyte selective electrode and the reference electrode are contacted with the sample and a signal representative of a potential drop between the analyte selective electrode and the reference electrode is measured.

This signal is then used for determining the concentration of the analyte of interest present in the fluid sample prior to the addition of the predetermined amount of the analyte of interest thereto.

The combination of the two former methods into a combined method ensures that low analyte concentrations which fall below the linear range of the detecting electrodes are detectable even under highest concentrations of interfering substances.

Figure 4:
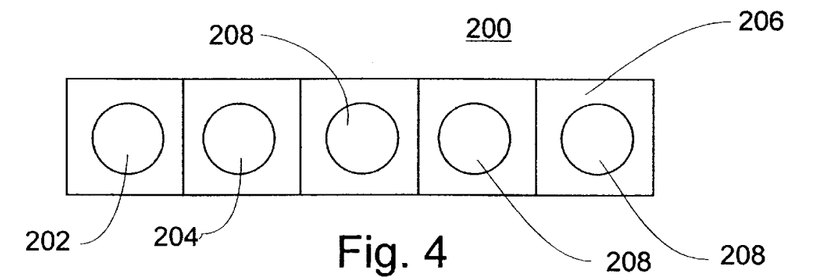
FIGS. 4 and 5 are simplified top views of kits according to the present invention.
Figure 5:
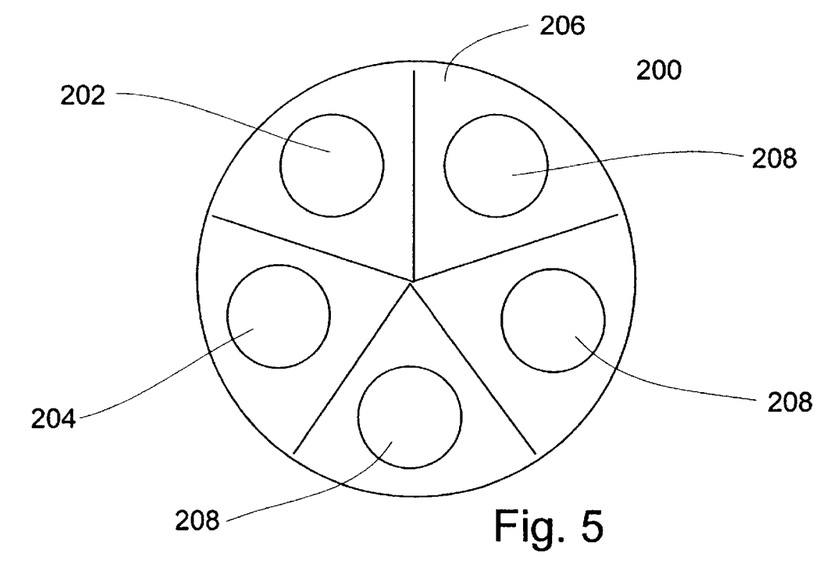

With reference to FIGS. 4 and 5, further according to the present invention there is provided a kit 200 useful in executing a potentiometric method for determining low concentration of an analyte of interest present in a fluid sample in a concentration optionally below its linear range of detection by the potentiometric method, wherein the sample includes known concentration(s) of at least one interfering substance(s).

Kit 200 includes a first container 202 which includes a predetermined amount of the analyte of interest, such that when the fluid sample is added to container 202 the total concentration of the analyte of interest present in the sample is within the linear range of its detection by the potentiometric method. Kit 200 further includes a second container 204 which includes an equilibrating and maintaining composition for equilibrating and maintaining (washing, keeping and, in case of ion transferring ionophore, also loading) an analyte selective electrode and a reference electrode being designed to determine the concentration of the analyte of interest in the fluid sample, the composition includes the interfering substance(s) in a concentration similar to their known concentration(s) in the sample.

Kit 200 preferably includes a holder 206 for holding containers 202 and 204 and preferably additional containers 208 including low and high concentration reference solutions including low and high concentrations of the analyte to be determined. Each of the high and low reference solutions preferably further includes the interfering substance(s) composition characterizing the equilibrating and maintaining composition according to the present invention. One additional container 208 preferably also includes the equilibrating and maintaining solution and serves for washing the electrodes after use and prior to keeping them in container 204 until further use.

According to a preferred embodiment of the present invention holder 206 is fragmented, such that a fragment thereof holding container 204 can be detached therefrom and serve for keeping the electrodes between uses, while the other kit components are disposed.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A potentiometric method for determining a concentration of an analyte of interest present in a fluid sample in concentration optionally below its linear range of detection, the method comprising the steps of:
   (a) adding to the sample a predetermined amount of the analyte of interest, such that a total concentration of the analyte of interest present in the sample is within the linear range of its detection;
   (b) contacting an analyte selective electrode being selective to the analyte of interest and a reference electrode with the sample;
   (c) measuring a signal representative of a potential drop between said analyte selective electrode and said reference electrode; and
   (d) using said signal for determining the concentration of the analyte of interest present in the sample prior to the addition of the predetermined amount of the analyte of interest.

2. The method of claim 1, wherein the analyte of interest is lithium.

3. The method of claim 1, wherein said fluid sample is a clinical sample.

4. The method of claim 3, wherein said clinical sample is selected from the group consisting of saliva, sera, plasma, urine, cerebro-spinal fluid and whole blood.

5. The method of claim 1, wherein said predetermined amount of the analyte of interest is added to the sample in a dry form.

6. The method of claim 5, wherein adding said predetermined amount of the analyte of interest to the sample is effected by pouring the sample into a container including said predetermined amount of the analyte of interest is said dry form.

7. The method of claim 1, further comprising the step adding to the sample a predetermined amount of at least one substance selected from the group consisting of anti-foam, detergent, surfactant and buffer.

8. A potentiometric method for determining a concentration of an analyte of interest present in a fluid sample in presence of at least one interfering substance of known concentration, the method comprising the steps of:
   (a) providing an analyte selective electrode being selective to the analyte of interest and a reference electrode, both electrodes being equilibrated with a solution including the at least one interfering substance in concentration similar to said known concentration;
   (b) contacting said analyte selective electrode and said reference electrode with the sample;
   (c) measuring a signal representative of a potential drop between said analyte selective electrode and said reference electrode; and
   (d) using said signal for determining the concentration of the analyte of interest present in the sample.

9. The method of claim 8, wherein the analyte of interest is lithium.

10. The method of claim 8, wherein fluid sample is a clinical sample selected from the group consisting of saliva, sera, plasma, urine, cerebro-spinal fluid and whole blood.

11. The method of claim 8, wherein the at least one interfering substance of known concentration is selected from the group consisting of magnesium, potassium, sodium and calcium.

12. A potentiometric method for determining low concentration of an analyte of interest present in a fluid sample in a concentration optionally below its linear range of detection in presence of at least one interfering substance of known concentration, the method comprising the steps of:
   (a) adding to the sample a predetermined amount of the analyte of interest, such that a total concentration of the analyte of interest present in the sample is within the linear range of its detection;
   (b) providing an analyte selective electrode being selective to the analyte of interest and a reference electrode both being equilibrated with a solution including the at least one interfering substance in concentration similar to said known concentration;
   (c) contacting said analyte selective electrode and said reference electrode with the sample;
   (d) measuring a signal representative of a potential drop between said analyte selective electrode and said reference electrode; and
   (e) using said signal for determining the concentration of the analyte of interest present in the fluid sample prior to the addition of the predetermined amount of the analyte of interest.

13. The method of claim 12, wherein the analyte of interest is lithium and said interfering substance is selected from the group consisting of sodium, calcium and potassium.

14. The method of claim 12, wherein said fluid sample is a clinical sample.

15. The method of claim 14, wherein said clinical sample is selected from the group consisting of saliva, sera, plasma, urine, cerebro-spinal fluid and whole blood.

16. The method of claim 12, wherein said predetermined amount of the analyte of interest is added to the sample in a dry form.

17. The method of claim 16, wherein adding said predetermined amount of the analyte of interest to the sample is effected by pouring the sample into a container including said predetermined amount of the analyte of interest is said dry form.

18. The method of claim 16, further comprising the step adding to the sample a predetermined amount of at least one substance selected from the group consisting of anti-foam, detergent, surfactant and buffer.

19. A device useful in executing a potentiometric method for determining a concentration of an analyte of interest present in a fluid sample in concentration optionally below its linear range of detection by the potentiometric method, the device comprising a container including a predetermined amount of the analyte of interest, such that when the fluid sample is added to the container a total concentration of the analyte of interest present in the sample is within the linear range of its detection.

20. The device of claim 19, wherein said predetermined amount of the analyte of interest is in a dry form.

21. The device of claim 19, wherein said predetermined amount of the analyte of interest is in a dry form and is dissolvably adhered to said container.

22. The device of claim 19, wherein said analyte of interest is lithium.

23. The device of claim 22, further comprising at least one substance selected from the group consisting of anti-foam, detergent, surfactant and buffer.

24. An electrode equilibrating and maintaining solution useful in equilibrating and maintaining an analyte selective electrode and a reference electrode, said analyte selective electrode and reference electrodes being designed to determine a concentration of an analyte of interest in a fluid sample including a known concentration of at least one interfering substance, the solution having a composition comprising the at least one interfering substance in a concentration similar to said known concentration of the at least one interfering substance in the sample.

25. The equilibrating and maintaining composition of claim 24, comprising about 2–40 mmole per liter calcium ions, about 0.2–4 mmole per liter magnesium ions, about 10–50 mmole per liter potassium ions and about 2–20 mmole per liter sodium ions, the composition is for determining a concentration of an analyte of interest in a saliva sample.

26. The equilibrating and maintaining composition of claim 25, comprising about 10 mmole per liter calcium ions, about 2.5 mmole per liter magnesium ions, about 40 mmole per liter potassium ions and about 8 mmole per liter sodium ions.

27. A kit useful in executing a potentiometric method for determining low concentration of an analyte of interest present in a fluid sample in a concentration optionally below its linear range of detection by the potentiometric method, the sample including a known concentration of at least one interfering substance, the kit comprising:

(a) a first container including a predetermined amount of the analyte of interest, such that when the fluid sample is added to the container a total concentration of the analyte of interest present in the sample is within the linear range of its detection; and (b) a second container including an equilibrating and maintaining solution for equilibrating and maintaining an analyte selective electrode and a reference electrode, said analyte selective electrode and reference electrodes being designed to determine the concentration of the analyte of interest in the fluid sample, said solution having a composition including the at least one interfering substance in concentration similar to the known concentration of the at least one interfering substance in the sample.

28. The kit of claim 27, further comprising:

(c) a third container containing a low concentration reference solution which includes a low concentration of the analyte to be determined; and (d) a fourth container containing a high concentration reference solution which includes a high concentration of the analyte to be determined;

wherein said low concentration reference solution and said high concentration reference solution may be employed for calibration.

29. The kit of claim 27, further comprising an additional amount of said equilibrating and maintaining solution, said additional amount employed for washing said electrode.

* * * * *